United States Patent [19]

Jones

[11] Patent Number: 4,660,413

[45] Date of Patent: Apr. 28, 1987

[54] APPARATUS AND METHOD FOR DETERMINING FLUID VISCOSITY AND DENSITY

[75] Inventor: Stanley C. Jones, Littleton, Colo.

[73] Assignee: Marathon Oil Company, Findlay, Ohio

[21] Appl. No.: 872,739

[22] Filed: Jun. 10, 1986

[51] Int. Cl.⁴ .............................................. G01N 11/00
[52] U.S. Cl. ....................................... 73/54; 73/32 R
[58] Field of Search .................... 73/54, 57, 58, 32 R, 73/861.57

[56] References Cited

U.S. PATENT DOCUMENTS

| | | | |
|---|---|---|---|
| 2,209,755 | 7/1940 | Beale | 73/57 |
| 2,348,732 | 5/1944 | Fischer | 265/11 |
| 2,348,733 | 5/1944 | Fischer | 265/44 |
| 2,426,393 | 8/1947 | Fischer | 73/56 |
| 2,800,019 | 7/1957 | Rumble | 73/209 |
| 3,277,916 | 11/1966 | Deming | 73/57 |
| 3,512,395 | 5/1970 | Valentik | 73/54 |
| 3,513,696 | 5/1970 | Blair | 73/148 |

FOREIGN PATENT DOCUMENTS

| | | | |
|---|---|---|---|
| 14164 | 8/1980 | European Pat. Off. | 73/54 |
| 780932 | 8/1957 | United Kingdom . | |

Primary Examiner—Stewart J. Levy
Assistant Examiner—Hezron E. Williams
Attorney, Agent, or Firm—Jack L. Hummel; Rodney F. Brown

[57] ABSTRACT

An apparatus and method for determining the viscosity and density of a fluid by circulating the fluid upward through a tube, having a cup positioned therein, at a fluid flow rate which suspends the cup in a stationary equilibrium position. Thereafter, a weight is added to the cup and a new fluid flow rate which suspends the weighted cup in the equilibrium position is determined. The density and viscosity of the fluid are determined as a function of the two fluid flow rate values and the physical characteristics of the apparatus.

22 Claims, 3 Drawing Figures

APPARATUS AND METHOD FOR DETERMINING FLUID VISCOSITY AND DENSITY

BACKGROUND OF THE INVENTION

1. Technical Field

The invention relates to an apparatus and method for simultaneously determining the viscosity and density of a fluid.

2. Description of Related Art

A number of apparatus and methods exist for measuring the density or viscosity of a fluid. U.S. Pat. Nos. 2,348,732 and 2,348,733 to Fischer and 2,800,019 to Rumble and British Pat. No. 780,932 to Vereinigte Glanzstoff-Fabriken A. G. employ a float within a vertically tapered tube to determine the viscosity or density of a flowing fluid. U.S. Pat. No. 2,426,393 to Fischer discloses an apparatus for measuring the viscosity of a fluid by comparing the relative position of two floats in a tube.

Other common apparatus for determining the viscosity of a fluid include falling ball, rolling ball and capillary tube viscometers. Falling and rolling ball viscometers do not determine absolute viscosity, but kinematic viscosity which is the ratio of the absolute viscosity to the density of the fluid. The apparatus have limited accuracy and range. They are subject to fouling, especially when used with crude oils that precipitate paraffinic or asphaltic materials.

Capillary tube viscometers are difficult to use with different fluids because of problems with cleaning and the long times required to reach equilibrium when changing fluids. The apparatus are extremely sensitive, especially at high line pressures, and require precise calibration of the differential pressure transducer which is often a source of error.

An alternative apparatus and method from those described above are needed for determining the viscosity and density of a fluid. An apparatus and method are needed which are accurate and easy to use, especially at high pressure and temperature.

SUMMARY OF THE INVENTION

The present invention provides an apparatus and method for simultaneously determining the viscosity and density of a flowing Newtonian fluid. The apparatus comprises a vertically aligned tube forming a fluid conduit. A flat-bottomed cup having a slightly smaller diameter than the tube is positioned therein to create a small annular flow channel between the tube and cup. End plugs are closely positioned in the tube above and below the cup to restrict vertical movement of the cup beyond the plugs, but enable free vertical movement between the plugs. The upper plug has a weight detachably affixed thereto which is capable of placement in the cup. Fluid in the tube is free to flow continuously across the length of the tube past the cup and plugs, the plugs having flow channels formed therethrough.

A fluid is conveyed through the tube by means of an external pump. The pump is regulated by sensors which determine the position of the cup in the tube and adjust the flow rate of the pump accordingly. "Flow rate" as used herein is defined as volumetric flow rate having units of volume per unit time.

The above-described apparatus is operated by pumping a fluid of interest into the bottom of the tube, past the cup and out the top of the tube. The fluid flow rate is regulated to suspend the cup in an equilibrium position between the upper and lower plugs. The equilibrium flow rate is reached by an iterative method wherein sensors locate the position of the cup relative to the plugs and relay signals to the pump. Pump flow rate is increased if the cup approaches or touches the lower plug and decreased if the cup approaches or touches the upper plug. Once the cup reaches equilibrium between the plugs, the equilibrium flow rate is recorded. The weight is then detached from the upper plug and drops into the cup. A second equilibrium flow rate for the weighted cup is determined in the same manner as described above. Given the equilibrium flow rates for the unweighted and weighted cup, the physical properties of the cup, including its dimensions and density, and the local value for the acceleration of gravity, the viscosity and density of the fluid are calculated.

The apparatus and process of the present invention are particularly suitable for use with Newtonian fluids at high temperature and pressures, for example fluids in a PVT cell. The apparatus and method provide relatively rapid and accurate fluid viscosity and density data.

DESCRIPTION OF PREFERRED EMBODIMENTS

Figure 2:
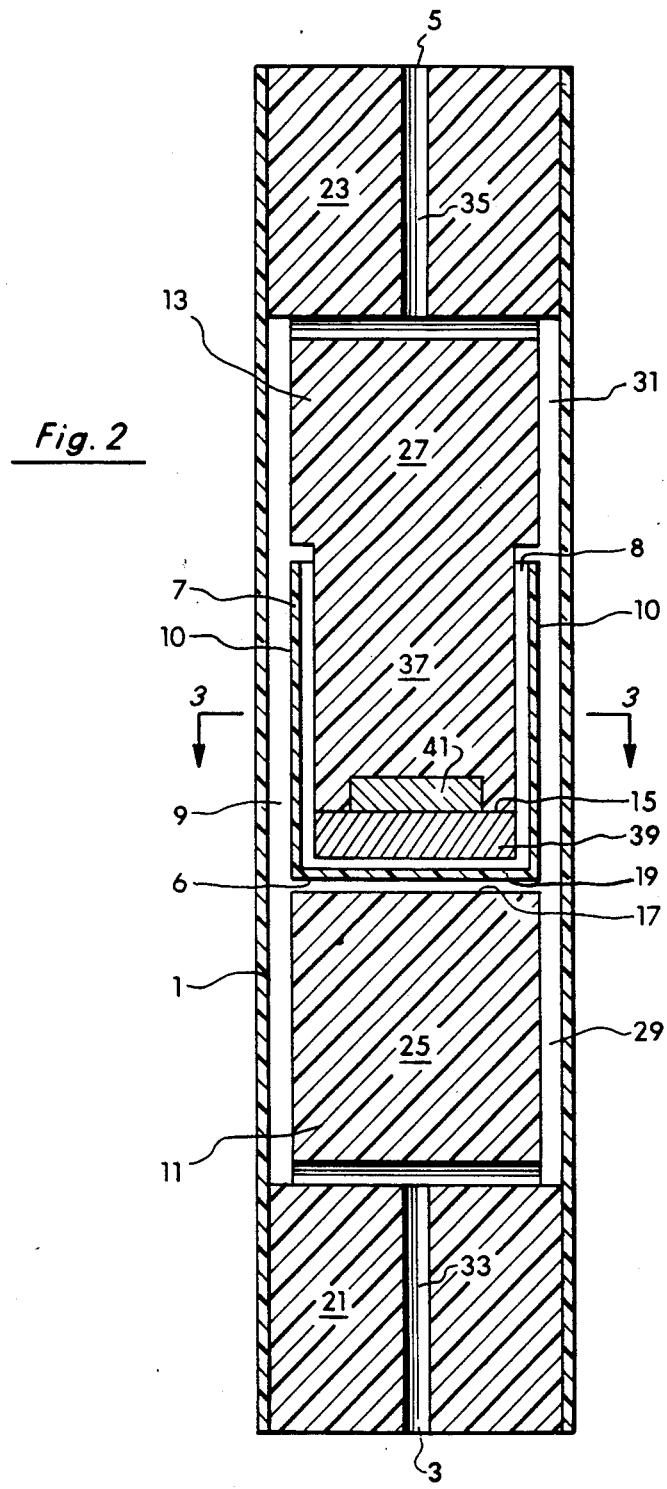
FIG. 2 is a cutaway side view of the tube and its contents.

The apparatus of the present invention is described below with reference to the embodiment of FIG. 2. FIG. 2 shows a vertically aligned tube 1 with a fluid inlet 3 at the bottom and a fluid outlet 5 at the top. The tube has a substantially uniform diameter along its entire length.

A cup 7, having a substantially flat bottom 6 and an open top 8, is positioned within the tube such that its sides 10 are substantially parallel to the wall of the tube. The external diameter of the cup is slightly smaller than the internal diameter of the tube to form a narrow annular flow channel 9 between the side 10 of the cup and the tube wall 1.

Vertical movement of the cup within the tube is restricted by two plugs 13, 11 positioned in the tube above and below the cup respectively. The substantially flat end faces of the upper and lower plugs 15, 17 converge in parallel planes to define a limited void space 19 through which fluid is free to flow and within which the cup 7 is free to move vertically.

The upper and lower plugs 13, 11, as shown in the embodiment of FIG. 2, comprise tiers which decrease in diameter as they approach the cup. The widest tiers of each plug 23, 21 furthest from the cup have an outside diameter substantially equal to the inside diameter of the tube such that substantially no fluid can pass between the plug at this point and the tube. The next descending tiers 27, 25 have an outside diameter less than the inside diameter of the tube, but substantially the same as the outside diameter of the cup 7. The tiers define annuli 29, 31 between themselves and the tube which are in direct fluid communication with the annular flow channel between the cup and tube. Continuous flow of fluids through the tube is enabled by a bore 35 through the widest tier of the upper plug 23 and a similar bore 33 through the widest tier of the lower plug 21.

The lower plug terminates at the flat end face 17 of tier 25 adjacent to and below the bottom of the cup 7. The upper plug 23 has an additional tier 37 which fits loosely within the thin sides 10 of the cup 7 because the outside diameter of the tier is less than the inside diameter of the cup. The upper plug 13 terminates at the flat end face 15 of this tier 37 adjacent to and above the top of the cup.

The upper plug 13 has a weight 39 removably affixed to its end face 15. The weight is sized to enable it to fit on the bottom of the cup. The weight is affixed to the upper plug by means such as a magnetic force wherein the weight comprises a magnetic material. An electromagnet 41 positioned in the upper plug 13 can be energized from an external power source to retain the weight on the plug. According to the process of the present invention the weight may be positioned on the bottom of the cup by deenergizing the electromagnet. The weight can subsequently be returned to its position on the upper plug by reenergizing the magnet.

As noted above, the space 19 between the plugs is relatively small to minimize the fluid holdup volume. For example, when the distance between the plugs is about 0.32 cm, the holdup volume is only about 1 cm$^3$ for a cup 2.54 cm high and 1.27 cm in outside diameter. The annulus between the cup and the tube is also small. The external diameter of the cup is generally in a range of about 97 to 99% of the internal diameter of the tube when measuring the viscosities of many common fluids, but may be below this range for extremely viscous liquids or above this range for gases.

It is advantageous to construct the cup, tube and end plugs from the same material so that the ratio of tube inner diameter to cup outer diameter is maintained substantially constant over a wide temperature range. This ratio, which is defined as $\kappa$, is an important dimensional parameter of the apparatus. Other dimensions of the apparatus which may change with temperature have a relatively insignificant effect on viscosity and density determinations.

Dimensional changes resulting from high fluid pressures can be minimized by pressurizing the outside of the tube to the same pressure as the inside of the tube. The cup, being hollow, is already hydrostatically balanced.

An exemplary material for construction of the apparatus is polyphenylene sulfide, such as that produced by International Polymer Corporation, 3434 Lang Road, Houston, Tex. 77092, U.S.A. under the trade name RYTON IPC-1837. The material has a density of 1.512 g/cm$^3$, a compressive strength of 165,600 kPa, a thermal coefficient of volumetric expansion of $2.52 \times 10^{-5}$ °C.$^{-1}$ and a useful life at temperatures exceeding 260° C.

Figure 1:
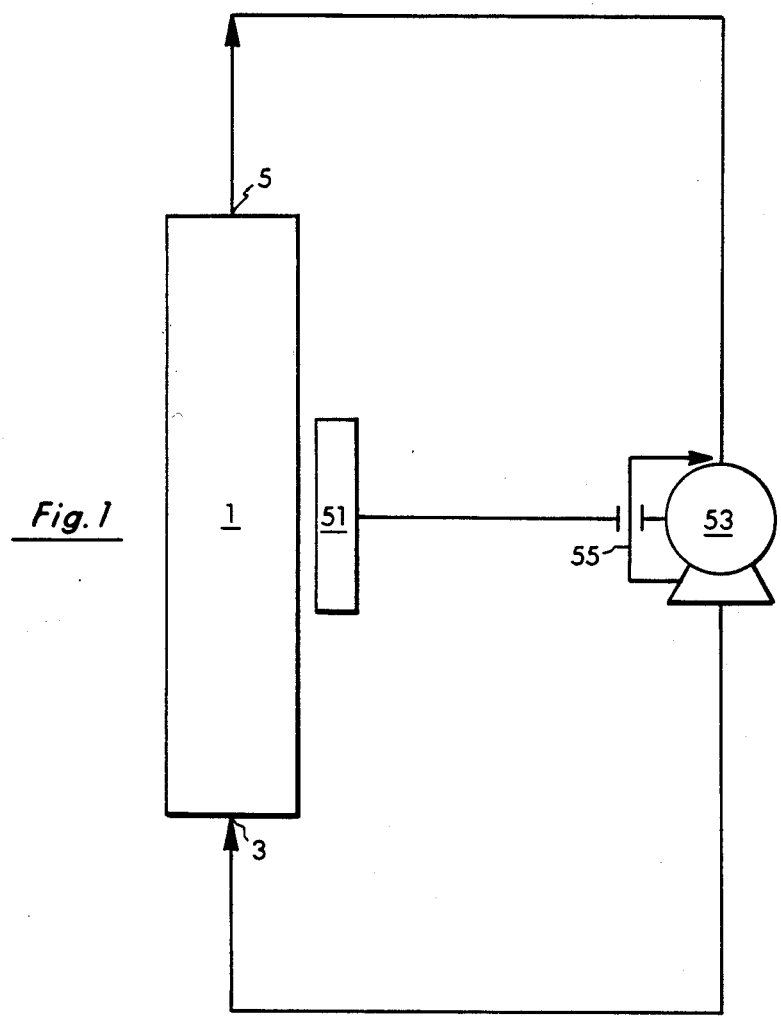
FIG. 1 is a schematic representation of the apparatus and method of the present invention.
Figure 3:
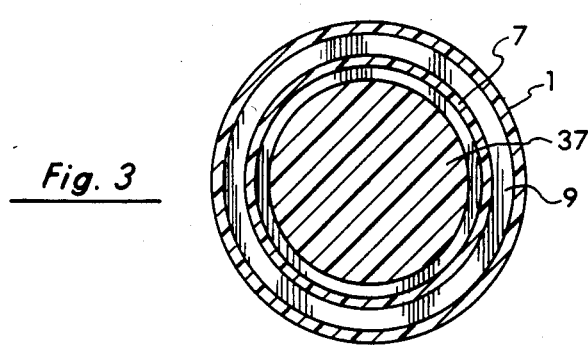
FIG. 3 is a cutaway top view of the tube and cup.

As shown in FIG. 1, a sensor 51 is positioned near the tube 1 to determine the position of the cup 7 during operation of the apparatus. The sensor communicates with a pump 53 used to circulate fluid through the tube and controls the pump flow rate as a function of the cup position. The apparatus may operate with either a contact-type sensor or a proximity sensor. An exemplary contact-type sensor is a go/no-go sensor such as a Hall effect switch. An exemplary proximity-type sensor is a proportional sensor such as an eddy current sensor.

Operation of the apparatus with a go/no-go sensor is accomplished by filling the tube with fluid while the pump is turned off and the weight is affixed to the upper plug. The bottom of the cup settles on the face of the lower plug and the sensor, detecting the contact, turns the pump on at a low flow rate. The flow rate of the pump is gradually and continuously increased until the sensor indicates the cup is no longer contacting the lower plug. At this point, the pump flow rate is held constant. A short time later the cup contacts the upper plug. The sensor, detecting the contact, gradually decreases the pump flow rate, but more slowly than the flow rate was previously increased. When the cup no longer contacts the upper end plug, the pump flow rate is held constant until the cup contacts the lower plug. Once again the pump flow rate is gradually increased at an incrementally slower rate when the cup contacts the lower plug. The process is continued, successively refining the pump flow rate, until the cup reaches an equilibrium position where it no longer contacts either plug at a substantially constant flow rate. The fluid flow rate at this point is recorded.

Thereafter, the weight is detached from the upper plug and drops into a position on the bottom of the cup. The fluid flow rate required to bring the weighted cup to equilibrium in the apparatus is determined in the same manner as described above and the fluid flow rate is recorded.

The fluid flow rate for equilibrium positions of the weighted and unweighted cup may also be determined using a proportional sensor in a manner similar to that described above. The sensor indicates the position of the cup as the fluid circulates through the apparatus at a given flow rate. The sensor regulates flow to a feedback loop 55 to the pump to effect proportional changes in the pump flow rate until the cup reaches the equilibrium position between the plugs. The proportional sensor enables a more rapid convergence to equilibrium than the go/no-go sensor.

Once the flow rates for the unweighted and weighted cup at equilibrium are determined using the apparatus of the present invention, the viscosity and density of the flowing fluid are both calculated. The following equations used to determine the density and viscosity of a fluid using the apparatus and method of the present invention are derived from a force balance on the cup at equilibrium:

$$\rho_f = \frac{W_w - [(Q_w/Q_c) - 1]W_c}{V_w - [(Q_w/Q_c) - 1]V_c} \quad (1)$$

$$\mu_f = \frac{V_c(\rho_c - \rho_f)gR^2[(1 + \kappa^2)\ln(1/\kappa) - 1 + \kappa^2]}{4hQ_c} \quad (2)$$

$$\mu_f = \frac{[V_c(\rho_c - \rho_f) + V_w(\rho_w - \rho_f)]gR^2[(1 + \kappa^2)\ln(1/\kappa) - 1 + \kappa^2]}{4hQ_w} \quad (3)$$

where:
  $\rho_f$ is the density of the fluid;
  $\mu_f$ is the absolute viscosity of the fluid;
  $Q_c$ is the fluid volumetric flow rate at equilibrium for the unweighted cup;
  $Q_w$ is the fluid volumetric flow rate at equilibrium for the weighted cup;
  $W_c$ is the weight of the unweighted cup;
  $W_w$ is the weight of the weighted cup;
  $V_c$ is the volume of the solid portion of the unweighted cup;

$V_w$ is the volume of the solid portion of the weighted cup;
$\rho_c$ is the density of the cup;
$\rho_w$ is the density of the weight;
$\kappa$ is the ratio of the cup outer diameter to tube inner diameter;
R is the radius from the tube axis to the inside tube wall;
h is the height of the cup; and
g is the local acceleration of gravity.

A sample calculation with the requisite equations is provided hereafter. The example demonstrates the practice and utility of the present invention but is not to be construed as limiting the scope thereof.

The apparatus of the present invention comprises a RYTON cup and a stainless steel weight and has the following dimensions and physical characteristics:

$W_c = 1.2649$ g
$W_w = 0.9856$ g
$V_c = 0.8366$ cm$^3$
$V_w = 0.1255$ cm$^3$
$\rho_c = 1.512$ g/cm$^3$
$\rho_w = 7853$ g/cm$^3$
$\kappa = 0.9800$
$R = 0.7128$ cm
$h = 2.540$ cm The local acceleration of gravity is 980.7 cm/sec$^2$.

A fluid is pumped through the tube of the apparatus while adjusting the pump flow rate until the unweighted cup reaches an equilibrium position between the two plugs in the tube. The fluid flow rate, $Q_c$, at this point is determined to be 5.0517 cm$^3$/min. The weight is then detached from the upper plug and placed in the cup. The equilibrium flow rate for the weighted cup, $Q_w$, is determined to be 12.1157 cm$^3$/min. The values for $Q_c$ and $Q_w$ are used in Equation (1) to calculate the density of the fluid to be 0.7500 g/cm$^3$. The density is then used in Equation (2) or (3) to calculate the viscosity of the fluid to be 0.200 cp.

While foregoing preferred embodiments of the invention have been described and shown, it is understood that all alternatives and modifications, such as those suggested and others, may be made thereto and follow in the scope of the invention.

I claim:

1. An apparatus for measuring the viscosity and density of a fluid comprising:
   a vertically aligned tube having a substantially uniform inside diameter;
   a suspendable cup, having a substantially flat closed bottom of a given thickness, a side wall defining an outside diameter less than the inside diameter of said tube, and an open top, said cup positioned within said tube to form an annular flow channel between said side wall and tube;
   stationary upper and lower plugs positioned in said tube above and below the flat bottom of said cup to restrict vertical movement of said cup, said plugs spaced a distance apart greater than the thickness of said cup bottom to form a space in fluid communication with said annular flow channel;
   a releasable weight affixable to said upper plug and able to fit within said cup;
   fluid passageways across said upper and lower plugs in fluid communication with said annular flow channel to enable a continuous flow of the fluid through said tube; and
   a pumping means for circulating the fluid through said tube at a given flow rate via said annular flow channels and fluid passageways.

2. The apparatus of claim 1 further comprising a sensing means in communication with said pumping means for locating the position of said cup in said tube and regulating the flow rate of the fluid through said tube in response to the position of said cup.

3. The apparatus of claim 1 wherein said fluid passageways across said upper and lower plugs comprise bores through said plugs.

4. The apparatus of claim 3 wherein said upper and lower plugs each comprises two tiers of differing diameters, a first tier furthest from said cup having an outside diameter substantially equal to the inside diameter of said tube and a second tier nearer said cup having an outside diameter less than the inside diameter of said tube to define an annulus between said tube and said second tier in fluid communication with said annular flow channel.

5. The apparatus of claim 1 wherein said outside diameters of said second tiers of said upper and lower plugs are substantially equal to one another and substantially equal to the outside diameter of said cup.

6. The apparatus of claim 5 wherein said upper plug is further comprised of a third tier positioned below said second tier and having an outside diameter less than the inside diameter of said cup, said third tier penetrating the open top of said cup.

7. The apparatus of claim 4 wherein said bores are through said first tiers.

8. The apparatus of claim 7 wherein said fluid passageways across said upper and lower plugs comprise said annuli between said tube and second tiers and said bores through said first tiers.

9. The apparatus of claim 6 further comprising a means for affixing said weight to said third tier.

10. The apparatus of claim 8 wherein said affixing means is an electromagnet and said weight comprises a magnetic material.

11. The apparatus of claim 1 wherein said tube, plugs and cup comprise the same material.

12. A method for determining the viscosity and density of a fluid comprising the steps of:
    circulating the fluid upward through an annular flow channel between a vertically aligned tube having a substantially uniform inside diameter and a cup, having a substantially flat closed bottom of a given thickness, a sidewall defining an outside diameter less than the inside diameter of said tube, and an open top, at a first fluid flow rate;
    determining said first fluid flow rate as that which freely suspends said cup at a substantially equilibrium position in said tube between an upper and a lower plug positioned respectively above and below said cup in said tube to restrict vertical movement of said cup;
    positioning a weight in said cup and circulating said fluid upward through said tube at a second fluid flow rate;
    determining said second fluid flow rate as that which freely suspends said cup and weight in said tube between said plugs at said substantially equilibrium position; and
    determining the viscosity and density of the fluid as a function of said first and second fluid flow rates and known physical characteristics of said cup, weight and tube.

13. The method of claim 12 wherein said cup is substantially free of contact with said upper or lower plug at said substantially equilibrium position.

14. The process of claim 12 wherein the vertical movement of said cup is restricted by a bottom tier of said upper plug having a smaller outside diameter than the inside diameter of said cup and penetrating said open top of said cup.

15. The process of claim 14 wherein said cup is suspended in said equilibrium position in a space between said lower plug and said bottom tier of said upper plug no greater than three times the thickness of the cup bottom.

16. The process of claim 12 wherein the ratio of the tube inner diameter to cup outer diameter is in the range of about 0.97 to about 0.99.

17. The process of claim 12 wherein said first fluid flow rate is determined with said weight attached to said upper plug.

18. The process of claim 17 wherein said weight is attached by an electromagnetic means.

19. The process of claim 18 wherein said weight is positioned in said cup by deenergizing said electromagnetic means.

20. The process of claim 12 wherein the fluid is circulated through said tube by a pumping means.

21. The process of claim 20 further comprising the step of regulating said fluid flow rate in said tube by a sensing means in communication with said pumping means.

22. The process of claim 21 wherein said sensing means locates the position of said cup in said tube and regulates said fluid flow rate in response to the position of said cup.

* * * * *

UNITED STATES PATENT AND TRADEMARK OFFICE
CERTIFICATE OF CORRECTION

PATENT NO. : 4,660,413

DATED : April 28, 1987

INVENTOR(S) : Stanley C. Jones

It is certified that error appears in the above-identified patent and that said Letters Patent is hereby corrected as shown below:

Col. 6, line 21: Delete "claim 1" and insert --claim 4--.
Col. 6, line 38: Delete "claim 8" and insert --claim 9--.

Signed and Sealed this

Eighth Day of November, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO.   : 4,660,413
DATED        : April 28, 1987
INVENTOR(S)  : Stanley C. Jones It is certified that error appears in the above-identified patent and that said Letters Patent is hereby corrected as shown below:

Col. 4, line 66:       Delete "weighted cup" and insert --weight--.
Col. 5, lines 1 and 2: Delete "weighted cup" and insert --weight--.
Col. 5, line 24:       Delete "7853" and insert --7.853--.

Signed and Sealed this

Twenty-sixth Day of June, 1990

Attest:

HARRY F. MANBECK, JR.

*Attesting Officer*   *Commissioner of Patents and Trademarks*